United States Patent
Nien et al.

(10) Patent No.: US 9,354,198 B2
(45) Date of Patent: May 31, 2016

(54) CALIBRATION METHOD, TEST STRIP AND CALIBRATION SYSTEM FOR BLOOD GLUCOSE OF BLOOD SAMPLE

(71) Applicant: DELBio, INC., Taoyuan County (TW)

(72) Inventors: Po-Chin Nien, Taoyuan County (TW); Cheng-Chuan Chen, Taoyuan County (TW); Chien-Yu Yin, Taoyuan County (TW); Chi-Yan Chen, Taoyuan County (TW)

(73) Assignee: DELBio, Inc., Taoyuan County (TW)

( * ) Notice: Subject to any disclaimer, the term of this patent is extended or adjusted under 35 U.S.C. 154(b) by 412 days.

(21) Appl. No.: 13/870,805

(22) Filed: Apr. 25, 2013

(65) Prior Publication Data

US 2013/0334064 A1    Dec. 19, 2013

Related U.S. Application Data

(60) Provisional application No. 61/659,148, filed on Jun. 13, 2012.

(51) Int. Cl.
 *G01N 27/327*    (2006.01)
 *G01N 27/416*    (2006.01)

(52) U.S. Cl.
 CPC ........ *G01N 27/4163* (2013.01); *G01N 27/3274* (2013.01)

(58) Field of Classification Search
 CPC .................................. G01N 27/3272–27/3274
 See application file for complete search history.

(56) References Cited

U.S. PATENT DOCUMENTS

| | | | | |
|---|---|---|---|---|
| 5,266,179 A | * | 11/1993 | Nankai et al. | 204/401 |
| 6,120,676 A | * | 9/2000 | Heller et al. | 205/777.5 |
| 7,276,147 B2 | * | 10/2007 | Wilsey | 205/792 |
| 2007/0131565 A1 | * | 6/2007 | Fujiwara et al. | 205/777.5 |
| 2011/0139634 A1 | * | 6/2011 | Chou et al. | 205/792 |

FOREIGN PATENT DOCUMENTS

TW           201132975 A        10/2011

* cited by examiner

*Primary Examiner* — Alexander Noguerola
(74) *Attorney, Agent, or Firm* — Muncy, Geissler, Olds & Lowe, P.C.

(57) ABSTRACT

A calibration method for blood glucose of blood sample comprises the following steps: applying a first voltage to a blood sample to obtain an original level of blood glucose of the blood sample; applying a second voltage to a blood sample to obtain a hematocrit index of the blood sample; and processing the hematocrit index and calibrating the original level of blood glucose of the blood sample. The absolute value of the first voltage is lower than 1 volt and is not equal to 0 volt. The absolute value of the second voltage is higher than or equal to 1 volt. A sensing current corresponding to the original blood level and the hematocrit index corresponding to blood sample are obtained by applying at least two-stage voltages in the specific range to the blood sample, thereby calibrating the original blood glucose according to the hematocrit index.

4 Claims, 7 Drawing Sheets

CALIBRATION METHOD, TEST STRIP AND CALIBRATION SYSTEM FOR BLOOD GLUCOSE OF BLOOD SAMPLE

CROSS REFERENCE TO RELATED APPLICATIONS

This Non-provisional application claims priority to U.S. provisional patent application with Ser. No. 61/659,148 filed on Jun. 13, 2012. This and all other extrinsic materials discussed herein are incorporated by reference in their entirety.

BACKGROUND OF THE INVENTION

1. Field of Invention

The present invention relates to a calibration method, a test strip, and a calibration system for blood glucose of blood sample, and more particularly, to a calibration method, a test strip, and a calibration system for blood glucose of blood sample with a two-stage voltage method and its applications.

2. Related Art

With the progress of technology and change of the human habits, the home health care gets more and more attention. The home health care is not only to monitor the real-time status of patients, but also to bring many inspection items from hospital to patients' home. The most common testing items comprise the blood glucose test, which is an important step to effectively control and treat diabetes.

However, the portable blood glucose meters used recently exist greater error value which is usually criticized by most users; and the most influential factor is the hematocrit (HCT) value of blood samples which is varied by different ages and situations. For example, newborn baby has a higher HCT resulting in underestimated glucose levels when measuring; the patients with dialysis have lower HCT resulting in overestimated glucose levels when measuring. Hence, many kinds of methods used for testing hematocrit of blood sample are developed.

The methods recently used for testing the hematocrit comprise fluid-velocity method, spectroscopic method, filtration by membrane, and especially the electrochemical method. The electrochemical method adapts electrochemical sensing strips to test the hematocrit of the testing solution, and then, to compensate the blood glucose with numerical calculation to make the testing result more close to the real value of the user.

However, some electrochemical method still remains some limitations; for example, it needs to apply direct current (DC) and alternating current (AC) alternatively. In addition, the conventional strip structure is too complicated to simplify the manufacturing procedure, nor to decrease the manufacturing time. Otherwise, the accuracy of the self-testing results by patients is still not enough because of the error affected by the hematocrit in the blood sample and the method of the blood glucose compensation.

Briefly speaking, the electrochemical method still needs to be improved, especially for the aspects of testing the hematocrit and blood glucose compensation. This might have a great influence to the self-testing blood glucose techniques. Therefore, it is an important subject to provide a calibration method, a test strip and a calibration system which are able to remove the disturbance of hematocrit and accurately rectifying blood glucose by simple manufacturing procedure.

SUMMARY OF THE INVENTION

In view of the foregoing, it is an objective of the present invention to provide a calibration method, a test strip and a calibration system which are able to remove the disturbance of hematocrit and accurately rectifying blood glucose.

To achieve the above, the present invention discloses a calibration method for blood glucose of blood sample comprises the following steps: applying a first voltage to a blood sample to obtain an original level of blood glucose of the blood sample; applying a second voltage to the blood sample to obtain a hematocrit index of the blood sample; and processing the hematocrit index and calibrating the original level of blood glucose of the blood sample. The absolute value of the first voltage is lower than 1 volt and is not equal to 0 volt. The absolute value of the second voltage is higher than or equal to 1 volt.

In one embodiment, the absolute value of the second voltage is in a range between 1 volt and 4 volts.

In one embodiment, the first voltage and the second voltage are direct current voltages.

In one embodiment, the step of processing the hematocrit index comprises obtaining a hematocrit according to a linear correlation formula.

In one embodiment, the calibration method includes: applying a third voltage to the blood sample to obtain a second hematocrit index of the blood sample.

To achieve the above, the present invention discloses a test strip for blood glucose of a blood sample including a bottom layer, two electrodes, a middle layer, a top layer and a reagent. The bottom layer has a reaction section. The two electrodes are disposed on the bottom layer and partially contacting the reaction section. The middle layer is disposed on the electrodes. The middle layer has an inlet section corresponding to the reaction section of the bottom layer. The top layer is disposed on the middle layer. The reagent is accommodated in the reaction section of the bottom layer. The reagent includes at least one electron transfer substance. The two electrodes are continuously applied with a first voltage and a second voltage therebetween. The absolute value of the first voltage is lower than 1 volt and is not equal to 0 volt. The absolute value of the second voltage is higher than or equal to 1 volt.

In one embodiment, the absolute value of the second voltage is in a range between 1 volt and 4 volts.

In one embodiment, the first voltage and the second voltage are direct current voltages.

To achieve the above, the present invention discloses a calibration system for blood glucose of a blood sample including a test strip, a converting module, a controlling module and a processing module. The test strip comprises a bottom layer, two electrodes, a middle layer, a top layer and a reagent. The bottom layer has a reaction section. The two electrodes are disposed on the bottom layer and partially contacting the reaction section. The middle layer is disposed on the electrodes. The middle layer has an inlet section corresponding to the reaction section of the bottom layer. The top layer is disposed on the middle layer. The reagent is accommodated in the reaction section of the bottom layer. The reagent includes at least one electron transfer substance. The two electrodes are continuously applied with a first voltage and a second voltage therebetween. The absolute value of the first voltage is lower than 1 volt and is not equal to 0 volt. The absolute value of the second voltage is higher than or equal to 1 volt. The converting module electrically connects to the test strip to convert a current signal generated by the test strip to a voltage signal. The controlling module electrically connects to the converting module to generate the voltage set previously to the converting module. The processing module electrically connects to the controlling module.

In one embodiment, the absolute value of the second voltage is in a range between 1 volt and 4 volts.

In one embodiment, the first voltage and the second voltage are direct current voltages.

As mentioned above, calibration method for blood glucose and test strip, and calibration system provided by the present invention are applied by injecting a blood sample into an electrochemical test strip, and processing the electrochemical reaction of blood sample with one working electrode and one auxiliary electrode disposed on the test strip. By this present invention, it obtains a sensing current corresponding to the original blood glucose level and the hematocrit index corresponding to blood sample by applying at least two-stage voltages of the specific ranges to the blood sample, and further calibrates the original blood glucose based on the hematocrit index to get an accurate blood glucose.

In the case of the test strip of the present invention, it defines a reaction section used for accommodating blood sample by the bottom layer, the middle layer and the top layer simultaneously. By disposing the bottom layer on the above-mentioned working electrode and the auxiliary electrode, the two electrodes are able to partially contact the reaction section and generate the electrochemical reaction to test the injecting blood sample. As mentioned above, the structure of the test strip provided by the present invention is not complicated, and is able to easily obtain the numerical result with simple steps, injecting the blood sample and conducting the electrochemical reaction. And then, calibrating the blood glucose by the tested linear correlation formula has the efficacies of easy processing and accurate calibration.

Compared with some conventional techniques, the calibration method for blood glucose and calibration system of the present invention applies at least two-stage voltages to the blood sample to detect the hematocrit in the blood sample for further blood glucose calibration. Especially the two-stage voltages are direct current voltages, and it can prevent the complicity of using direct current voltage and alternating current voltage simultaneously in previous arts. The present invention is advantageous for disposability, decreasing the possibility of the qualitative change and contamination of the testing sample, and further preventing the pre-washing and preprocessing.

BRIEF DESCRIPTION OF THE DRAWINGS

The present invention will become more fully understood from the subsequent detailed description and accompanying drawings, which are given by way of illustration only, and thus are not limitative of the present invention and wherein.

DETAILED DESCRIPTION OF THE INVENTION

The present invention will be apparent from the following detailed description, which proceeds with reference to the accompanying drawings, wherein the same references relate to the same elements.

Figure 1:
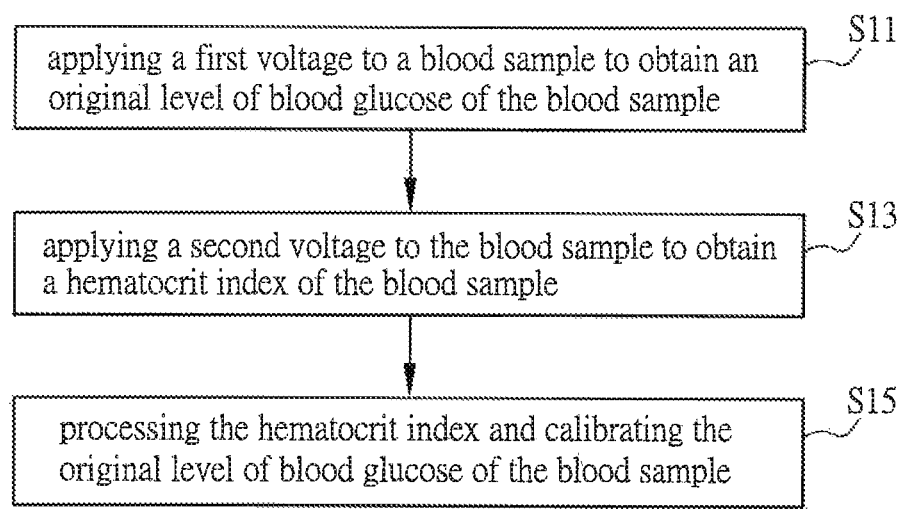
FIG. 1 is a flow chart showing the steps of the calibration method for blood glucose of blood sample.

FIG. 1 is a flow chart showing the steps of the calibration method for blood glucose of blood sample. The above calibrating method is called "the method" for clearly depicting in this embodiment. With reference to FIG. 1, the method comprises the following steps: applying a first voltage to a blood sample to obtain an original level of blood glucose of the blood sample (S11); applying a second voltage to the blood sample to obtain a hematocrit index of the blood sample (S13); processing the hematocrit index and calibrating the original level of blood glucose of the blood sample (S15). The absolute value of the first voltage is lower than 1 volt and is not equal to 0 volt. And the absolute value of the second voltage is higher than or equal to 1 volt.

To more explicitly illustrate the details of the methods of the present invention, the following takes an apparatus and whole blood as solution sample for example, and first illustrates the composition and the structure of the apparatus. Then, the method of the present invention will be specifically demonstrated based on the apparatus. However, the following description is for explicitly explanation, and is not meant to be construed in a limiting sense.

Figure 2A:
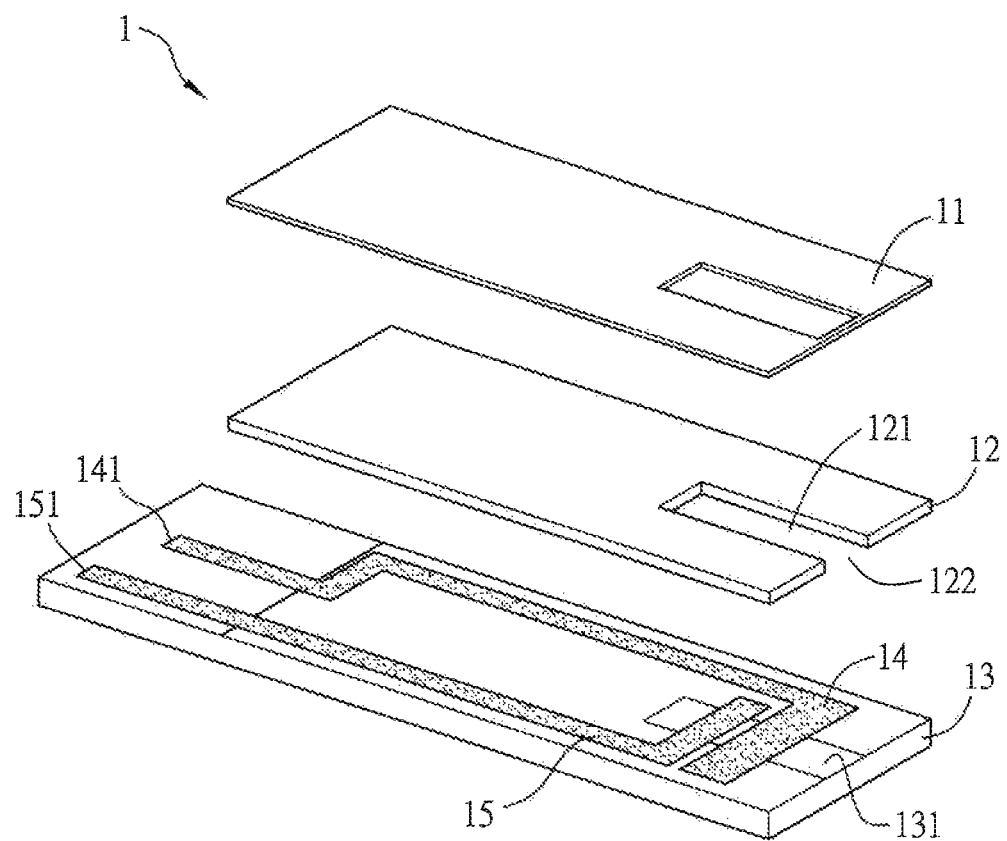
FIG. 2A is a decomposition view of a test strip for blood glucose of blood sample according to one embodiment of the present invention.

FIG. 2A is a decomposition view of a test strip for blood glucose of blood sample according to one embodiment of the present invention. With reference to FIG. 2A, in one embodiment, the test strip 1 comprises a top layer 11, a middle layer 12, two electrodes and a bottom layer 13 in an order from top to bottom. However, the structure of the test strip 1 mentioned above is not for limitation. The order and the relative correlation can be altered, or even adding other elements in the structure.

The bottom layer 13 is an electrically insulated substrate including but not limited for polyvinyl chloride, polystyrene, polyester, polycarbonate, polyether, polyethylene, polypropylene, polyethylene terephthalate, silica or aluminum oxide. The two electrodes arc working electrode 14 and auxiliary electrode 15. In this embodiment, the electrode structure is formed by screen printing in order to print the required pattern. The working electrode 14 and the auxiliary electrode 15 are not limited to carbon, single metal, alloy, or other conductive materials. Otherwise, the relative position, the pattern, and the size of the working electrode 14 and the auxiliary electrode 15 are not meant to be construed in a limiting sense.

With reference to FIG. 2A, one end of the bottom layer 13 has an anode 141 and a cathode 151 formed by the working electrode 14 and the auxiliary electrode 15, respectively. Likewise, the relative correlation of the anode 141 and the cathode 151 are formed according to the electrochemical cells and the direction electrons flow, and are not limited.

The other end of the bottom layer 13 has a reaction section 131. The two electrodes are at least partially disposed and covering the reaction section 131. In detail, by setting the middle layer 12 which containing an inlet section 121 relative to the reaction section 131 on the bottom layer 13, the combination of the middle layer 12 and the bottom layer 13 is able to define a space for accommodating blood sample. Thus, when blood sample is injected from the inlet section 121 of the middle layer into the reaction section 131, the working electrode 14 and the auxiliary electrode 15 are able to contact the blood sample, and further conduct the electrochemical reaction. The electrochemical reaction technique is well-understood by the person having ordinary skill in the art, and is not repeated here.

The detailed content related to the present invention of the electrochemical reaction technique mentioned above roughly comprises fixing a reagent on the reaction section 131, making it react with a substance in a solution and detecting the product as an electrical signal. In this embodiment, the solution to be tested is human whole blood, and the substance to be tested is hematocrit. The reagent used in the present invention is at least including an electron transfer substance. The electron transfer substance mentioned here can be tetrathiafulvalene, tetracyanoquinodimethan, meldola blue, Potassium ferrocyanide, ferrocene or ferrocenedicarboxylic acid, and is not for limitation. Otherwise, the reagent used in the present invention also comprises enzyme able to react with the substance to be tested, polymers or stabilizer.

Figure 2B:
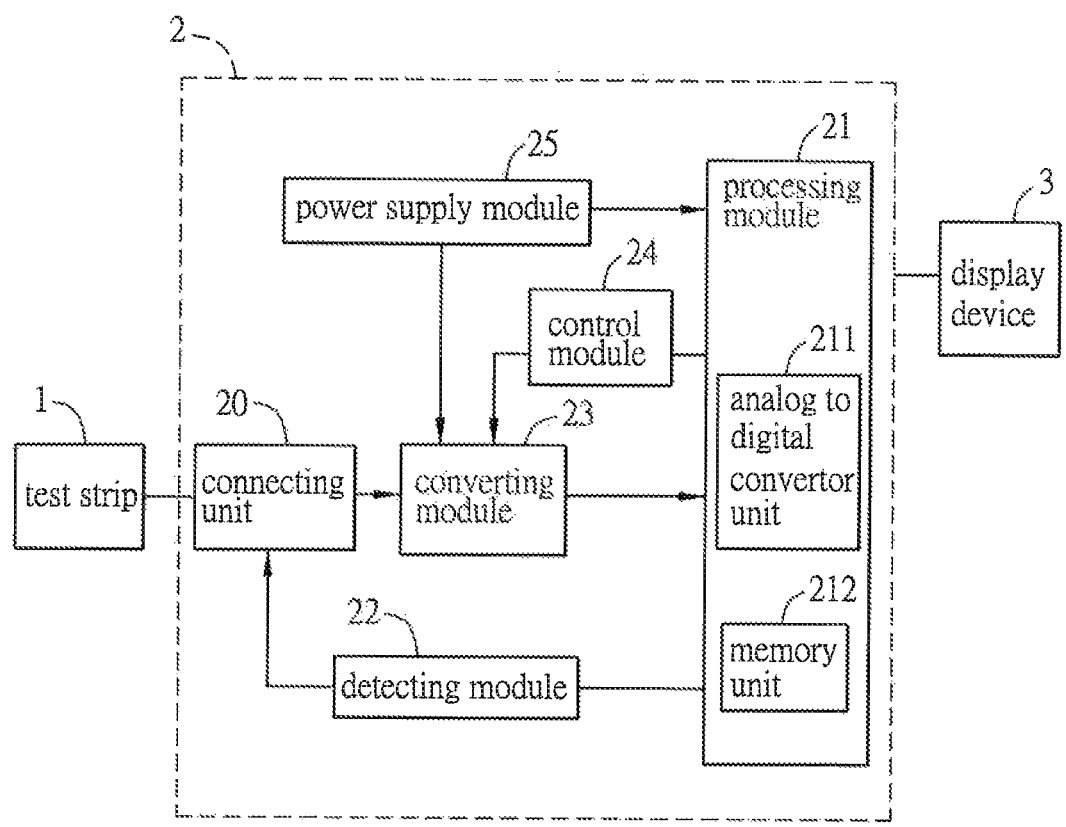
FIG. 2B is a function block diagram of a measuring device applied with the test strip in FIG. 2A.

FIG. 2B is a function block diagram of a measuring device applied with the test strip in FIG. 2A. With reference to FIG. 2A and FIG. 2B, the test strip 1 is electrically connected to a measuring device 2. In detail, the test strip 1 is disposed in a connecting unit 20 of the measuring device 2. The connecting unit 20 is a tank able to accommodate the test strip 1. Thus, the size and the shape of the connecting unit 20 are based on the test strip 1, and are not for limitation.

In one embodiment, the measuring device 2 further comprises a processing module 21, a detecting module 22, a converting module 23, a controlling module 24, and a power supply module 25. The detecting module 22 detects whether the test strip is inserted into the connecting unit 20 or not, and reports to the processing module 21. After the insertion of the test strip 1, the converting module 23 converts the current signal generated by the test strip 1 to the voltage signal, and delivers to the processing module 21 for the following calculation and determination. In this embodiment, due to the need of two-stage voltages application to the blood sample in the test strip 1, the controlling module 24 of the measuring device 2 is controlled by processing module 21 and generates the voltages in the specific range to the converting module 23. In addition, the voltage of the measuring device 2 is powered by the power supply module 25.

Particularly, the connecting correlation and the composition of each element in the measuring device 2 are not meant to be construed in a limiting sense. The test strip 1 is electrically connected to the measuring device 2. The memory unit 212 of the processing module 21 saves a plurality of linear correlation data which supplies for the processing module 21 to calculating the hematocrit tested from the blood sample and the calibrated blood glucose. Finally, the display device 3 shows the calibrated blood glucose.

As mentioned above, in the actual operation, as the test strip 1 is inserted into the measuring device 2 and the blood sample is injected into the reaction section 131 of the test strip, the detecting module 22 will report to the processing module 21. The processing module 21 further indicates the controlling module 24 to apply a voltage in specific range to the test strip 1. In the step S11 of FIG. A, the controlling module 24 indicates the converting module 23 to apply a first voltage to the working electrode 14 in order to generate a first current between the working electrode 14 and the auxiliary electrode 15. The first current is converted by the converting module 23 so as to form a first voltage curve. When the first voltage curve is delivered back to the processing module 21, the analog to digital convertor unit 211 processes the first voltage curve according to the data in the memory unit 212 to obtain the original blood glucose of the blood sample.

The original blood glucose tested by the step S11 is referred to the value which is not calibrated by the hematocrit index. The hematocrit is referred to the containing ratio (%) of red blood cell in the amount of blood. The blood glucose determined by portable meter may vary with the hematocrit. For most human body, the standard hematocrit is around 42%. When the hematocrit is higher than 42%, the detected blood glucose may be lower than the real blood glucose; on the contrary, when the hematocrit is lower than 42%, the detected blood glucose may be higher than the real blood glucose. Hence, in order to obtain the more accurate blood glucose testing result, the identification of the hematocrit is needed. Then, the compensation of the blood glucose according to hematocrit is processed.

As mentioned above, most techniques are not able to obtain accurate hematocrit, or even the blood glucose and the hematocrit through complicated steps and calibration. However, in the present invention, the step S13 is applying a second voltage to the blood sample to get a hematocrit index of the blood sample.

In the step S13, the processing module 21 indicates the controlling module 24 to apply a second voltage on the working electrode to generate a second current between the working electrode 14 and the auxiliary electrode 15. The second current is converted by the converting module 23 so as to form a second voltage curve. When the second voltage curve is delivered back to the processing module 21, the analog to digital convertor unit 211 processes the second voltage curve according to the data in the memory unit 212 to obtain the hematocrit index of the blood sample for compensation. But the techniques and the implementation details of the calibration method have been disclosed by the above-mentioned description, and are not repeated here.

In detail, the absolute value of the first voltage applied to blood sample by the converting module 23 is lower than 1 volt but not to 0 volt. That is, the first voltage may be 0.3 volts lasting for 3 seconds. The absolute value of the second voltage applied in the step S13 is higher than 1 volt, or equals to 1 volt. For example, the second voltage is 3 volts lasting for 3 seconds. That is, the values of the two-stage voltages are divided by 1. Particularly, the first voltage is preferably 0.3 volts, and the second voltage is preferably in a range between 1 volt and 4 volts, and more preferably 3 volts. With regard to the applying time of both the first voltage and the second voltage, 0.5 seconds to 5 seconds is preferable, and 3 seconds is much more preferable. In addition, the two-stage voltages are not limited to divide by volt. Otherwise, the first voltage and the second voltage are both direct current voltage. Contrary to some conventional techniques using direct current and alternate current voltages alternatively, the present invention is advantageous for its simplicity of the test process.

Figure 3:
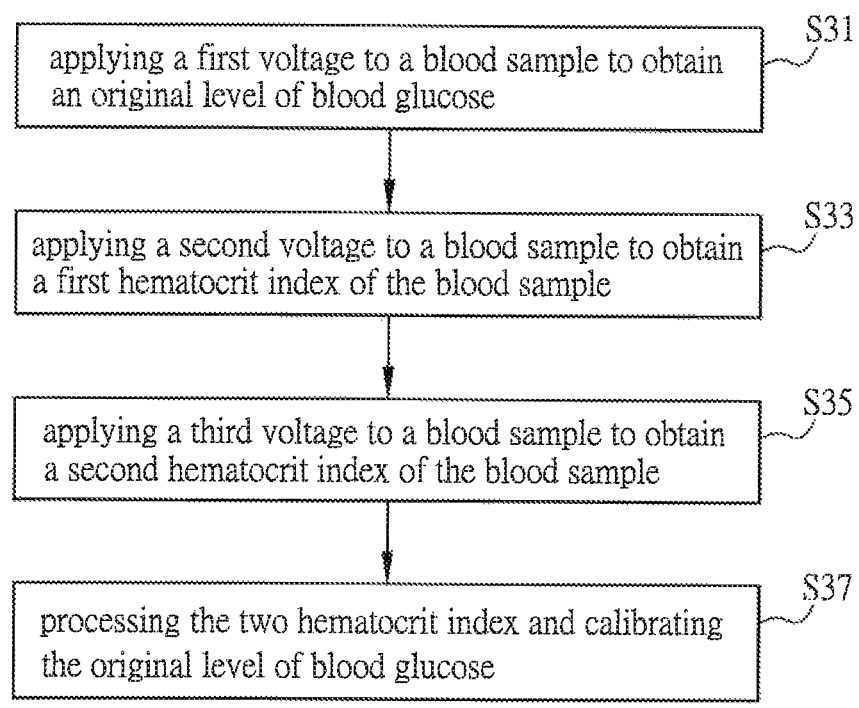
FIG. 3 is a flow chart showing the steps of the calibration method for blood glucose of blood sample according to the present invention.

FIG. 3 is a flow chart showing the steps of the calibration method for blood glucose of blood sample according to the present invention. With reference to FIG. 2B and FIG. 3, in this embodiment, the method comprises the following steps: applying a first voltage to a blood sample to obtain an original level of blood glucose (S31); applying a second voltage to a blood sample to obtain a first hematocrit index of the blood sample (S33); applying a third voltage to a blood sample to obtain a second hematocrit index of the blood sample (S35); processing the two hematocrit index and calibrating the original level of blood glucose (S37). But the techniques and the implementation details of the calibration method have been disclosed by the above-mentioned description, and are not repeated here.

Particularly, in the step S35, the controlling module 24 further applies a third voltage on the working electrode 14 to generate a third current curve between the working electrode 14 and the auxiliary electrode 15. The third current curve is converted by the converting module 23 so as to form a second voltage curve. When the third voltage curve is delivered back to the processing module 21, the analog to digital convertor unit 211 processes the third voltage curve and the second voltage curve according to the data in the memory unit 212 to obtain the hematocrit index corresponding to the blood sample for compensation by the hematocrit index.

In this embodiment, the value and the applying time of the third voltage may be but not limited to 1 volt for 0.2 second, 0.5 volts for 0.1 seconds, or 0.3 volts for 0.3 seconds. And the applying times and voltages, are not meant to be construed in a limiting sense. In other embodiments, the calibration methods may further include a fourth voltage, fifth voltage application after the third one, or even an $n^{th}$ voltage application. But the condition of other voltage applications after the third one have to adjusted with the third voltage application.

In addition, as mentioned above, with the multi-stage voltage application may assist the analog to digital convertor unit 211 of the processing module 21 to obtain more accurate blood glucose testing result. On the whole, with the continuous multi-stage voltage application, the present invention is able to obtain the blood glucose by original blood glucose and a plurality of hematocrit index, further saving manpower, material resource and time. Preferably, the present invention provides more accurate test result of the blood glucose.

The present invention further provides a calibration system of the blood glucose of blood sample. But the techniques, the implementation details and the elements of the system have been disclosed by the above-mentioned description, and are not repeated here.

The following and accompanying figures take a number of experiments for examples to describe the main details of the calibration method for blood glucose of blood sample and the practical applying method, and the effect of the implantation of the composition in accordance with the embodiments of the present invention.

The obtaining method of blood sample of the present invention comprises: collecting the venous blood with the blood collection tube (Heparin Green) and rolling for 30 minutes for well-mixing with oxygen on the roller.

Experiment 1: Obtaining the linear correlation of hematocrit index to hematocrit 20% glucose solution was added into the blood sample, rolling for 30 minutes. After the rolling, different samples with required hematocrit content are centrifugated and prepared. The test will be done after well-mixing. Then, the hematocrit index was calculated according to the test result. The result is referred to FIG. 4.

Figure 4:
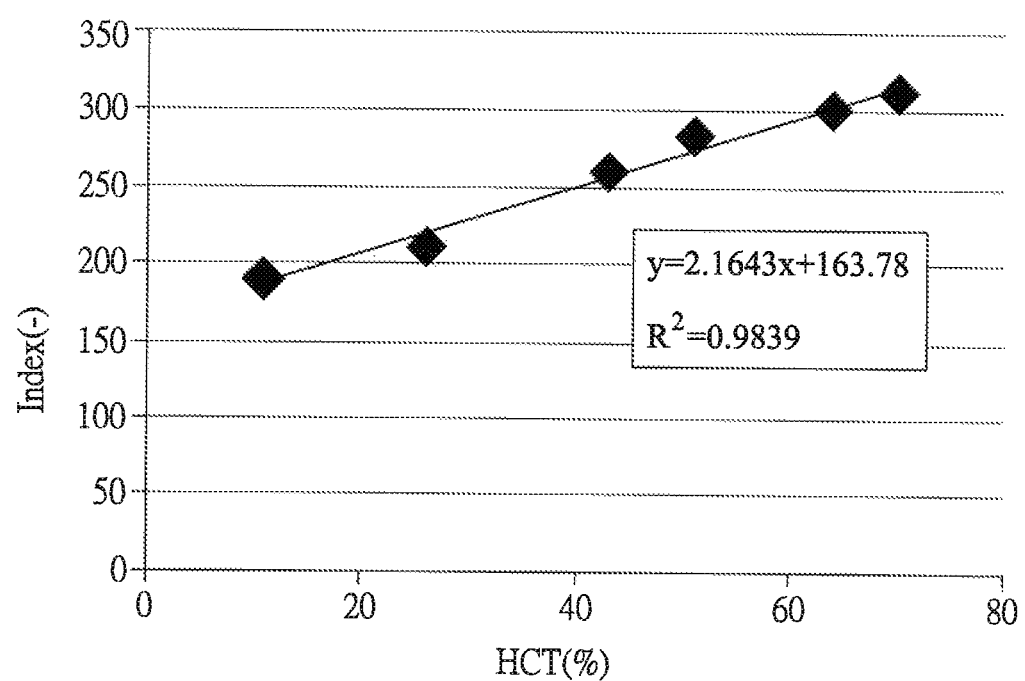
FIG. 4 is a linear correlation figure of the hematocrit index and the hematocrit.

FIG. 4 shows that the hematocrit index and the hematocrit have a linear correlation. Based on the above-mentioned linear correlation and the hematocrit index, the hematocrit can be obtained.

Experiment 2: Linear regression distribution correlation of hematocrit index with different blood glucose concentrations.

20% glucose solution was added into the blood sample for different amount, rolling for 30 minutes and testing. After the test, the blood sample was centrifugated and plasma portion of the blood sample was collected. The glucose concentration of plasma portion was determined by a standard measuring equipment. The result is referred to FIG. 5.

Figure 5:
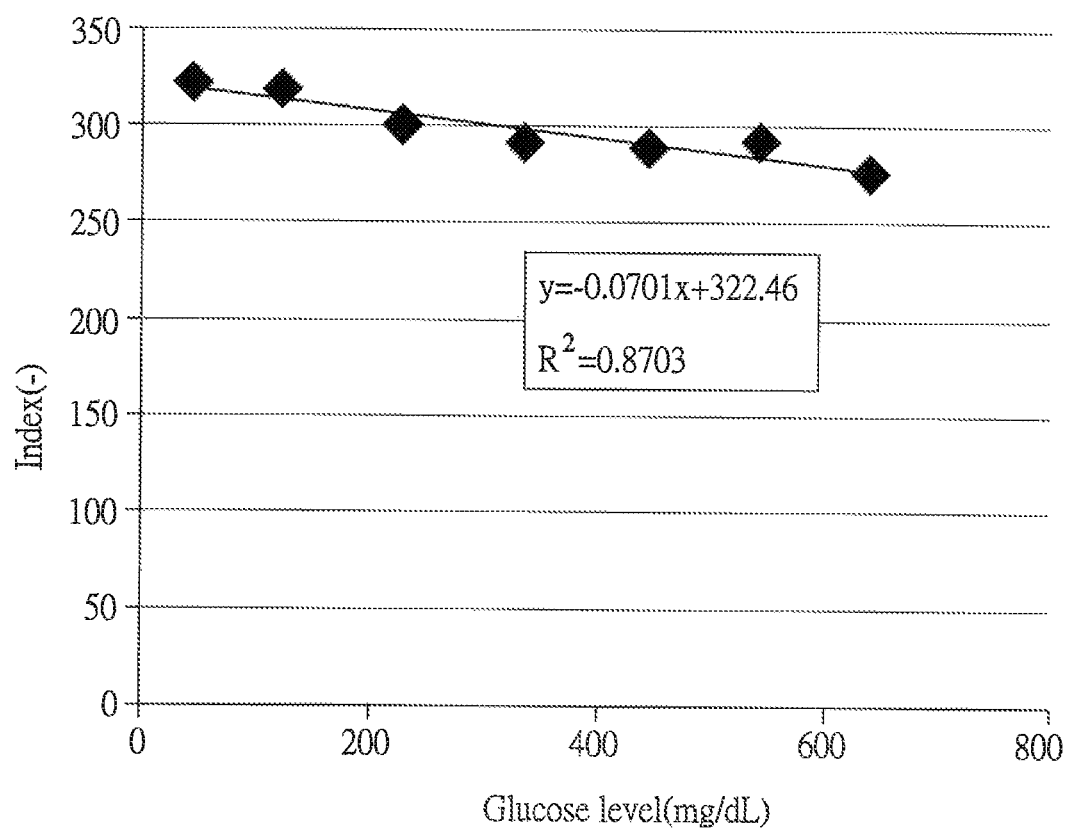
FIG. 5 is a linear regression distribution correlation of hematocrit index with different blood glucose concentrations.

As shown in FIG. 5, the glucose concentration has slight influence on the hematocrit index.

Experiment 3: Compensating the blood glucose with the hematocrit

20% glucose solution was added into the blood sample, rolling for 30 minutes. After the rolling, different samples required hematocrit content are centrifugated and prepared. The test will be done after well-mixing. Then, the hematocrit index was calculated according to the test result.

Figure 6:
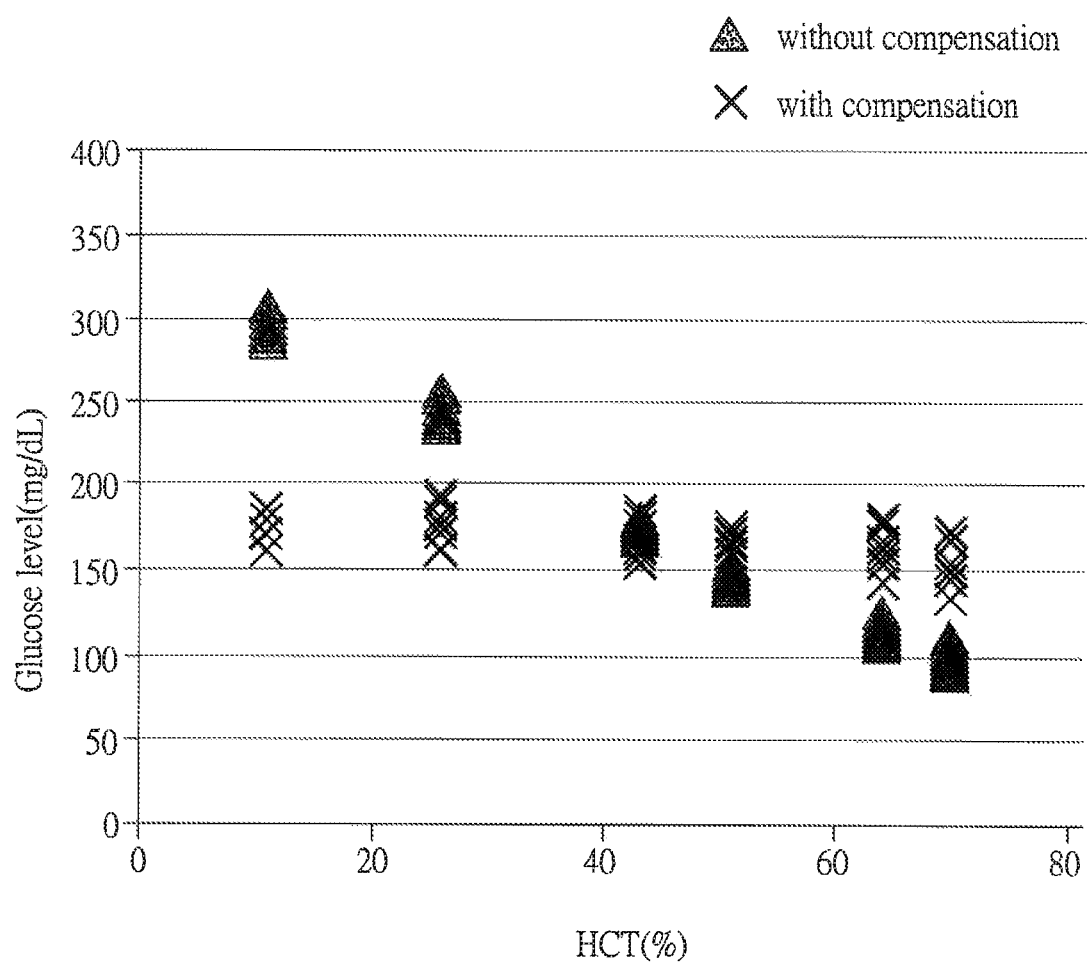
FIG. 6 shows the bias ratio before and after the compensation of blood glucose based on hematocrit index.

FIG. 6 shows the comparison of the blood glucose with compensation group (X) and the blood glucose without compensation group (Δ). Obviously, the blood glucose without compensation is able to be substantially compensated to the normal value (HCT=42%). That is, the method is able to prevent the disturbance of the hematocrit to the system.

It can be seen that the method of the present invention is able to effectively detect the hematocrit of blood sample, and further to complete the calibration of the blood glucose.

As mentioned above, calibration method for blood glucose of blood sample and test strip and calibration system provided by the present invention are applied by injecting a blood sample into a electrochemical test strip, and processing the electrochemical reaction of blood sample with one working electrode and one auxiliary electrode disposed on the test strip. By this present invention, it obtains a sensing current corresponding to the original blood glucose level and the hematocrit index corresponding to blood sample by applying at least two-stage voltages of the specific range to the blood sample, and further calibrates the original blood glucose based on the hematocrit index to get an accurate blood glucose.

In the case of the test strip of the present invention, it defines a reaction section used for accommodating blood sample by the bottom layer, the middle layer and the top layer simultaneously. By disposing the bottom layer on the above-mentioned working electrode and the auxiliary electrode, the two electrodes are able to partially contact the reaction section and generate the electrochemical reaction to test the injecting blood sample. As mentioned above, the structure of the test strip provided by the present invention is not complicated, and is able to easily obtain the numerical result with simple steps injecting the blood sample and conducting the electrochemical reaction. And then, calibrating the blood glucose with the tested linear correlation equation has the efficacies of easy processing and accurate calibration.

Compared with some conventional techniques, the calibration method for blood glucose and calibration system of the present invention applies at least two-stage voltages to the blood sample to detect the hematocrit in the blood sample for further blood glucose calibration. Especially the two-stage voltages are direct current voltages, and it can prevent the complicity of using direct current voltage and alternating current voltage simultaneously in previous arts. The present invention is advantageous for disposability, decreasing the possibility of the qualitative change and contamination of the testing sample, and further preventing the pre-washing and preprocessing.

Although the invention has been described with reference to specific embodiments, this description is not meant to be construed in a limiting sense. Various modifications of the disclosed embodiments, as well as alternative embodiments, are apparent to persons skilled in the art. It is, therefore, contemplated that the appended claims will cover all modifications that fall within the true scope of the invention.

What is claimed is:

1. A calibration method for blood glucose of blood sample, comprising the steps of:
    providing a test strip, wherein the test strip comprises only two electrodes and only one reaction section, and each of the two electrodes is at least partially disposed on and covering the reaction section;
    injecting a blood sample into the reaction section to contact the two electrodes;

applying a first voltage to the blood sample between the two electrodes to obtain an original level of blood glucose of the blood sample;

applying a second voltage to the blood sample between the two electrodes to obtain a hematocrit index of the blood sample; and processing the hematocrit index and calibrating the original level of blood glucose of the blood sample, wherein the absolute value of the first voltage is lower than 1 volt and is not equal to 0 volt, and the absolute value of the second voltage is higher than or equal to 1 volt, and the first voltage and the second voltage are direct current voltages.

2. The calibration method according to claim 1, wherein the absolute value of the second voltage is in a range between 1 volt and 4 volts.

3. The calibration method according to claim 1, wherein the step of processing the hematocrit index comprises obtaining a hematocrit according to a linear correlation formula.

4. The calibration method according to claim 1, further comprising a step of:

applying a third voltage to the blood sample between the two electrodes to obtain a second hematocrit index of the blood sample.

* * * * *